(12) United States Patent
Zhang (10) Patent No.: US 9,332,917 B2
(45) Date of Patent: May 10, 2016

(54) SYSTEM FOR NON-INVASIVE CARDIAC OUTPUT DETERMINATION

(71) Applicant: Hongxuan Zhang, Palatine, IL (US)

(72) Inventor: Hongxuan Zhang, Palatine, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 94 days.

(21) Appl. No.: 13/743,441

(22) Filed: Jan. 17, 2013

(65) Prior Publication Data

US 2013/0218038 A1    Aug. 22, 2013

Related U.S. Application Data

(60) Provisional application No. 61/601,697, filed on Feb. 22, 2012.

(51) Int. Cl.

| | |
|---|---|
| *A61B 5/029* | (2006.01) |
| *A61B 5/00* | (2006.01) |
| *A61B 5/021* | (2006.01) |
| *A61B 5/0205* | (2006.01) |
| *A61B 5/0456* | (2006.01) |
| *A61B 5/053* | (2006.01) |
| *A61B 5/1455* | (2006.01) |

(52) U.S. Cl.
CPC .................. *A61B 5/029* (2013.01); *A61B 5/021* (2013.01); *A61B 5/02055* (2013.01); *A61B 5/0456* (2013.01); *A61B 5/053* (2013.01); *A61B 5/14551* (2013.01); *A61B 5/7264* (2013.01); *A61B 5/7285* (2013.01)

(58) Field of Classification Search
CPC ...... A61B 5/29; A61B 5/0464; A61B 5/0468; A61B 5/021; A61B 5/02055; A61B 5/7264; A61B 5/7267

USPC ........................................... 600/526, 521, 516
See application file for complete search history.

(56) References Cited

U.S. PATENT DOCUMENTS

| | | | |
|---|---|---|---|
| 4,834,107 | A | 5/1989 | Warner |
| 5,025,795 | A | 6/1991 | Kunig |
| 5,101,825 | A | 4/1992 | Gravenstein et al. |
| 5,533,511 | A | 7/1996 | Kaspari et al. |
| 5,797,395 | A | 8/1998 | Martin |

(Continued)

OTHER PUBLICATIONS

Pier Giuseppe Agostoni, et al., "Non-invasive measurement of stroke volumeduring exercise in heart failure patients", clinical Science (2000) 98, 545-551.

(Continued)

*Primary Examiner* — William Levicky (57) ABSTRACT

A method determines cardiac output or stroke volume by receiving signal data representing multiple parameters of a patient concurrently acquired over a particular time period and comprising at least one of, (a) a parameter derived from an ECG waveform of the patient, (b) a parameter derived from a blood pressure signal of the patient, (c) a parameter derived from signal data representing oxygen content of blood of the patient and (d) a parameter derived from a patient cardiac impedance value. A selected parameter of the multiple concurrently acquired parameters is used in calculating a heart stroke volume of the patient comprising volume of blood transferred through the blood vessel in a heart cycle, in response to, a combination of a weighted summation of values of the selected parameter over the particular time period. Data representing the calculated heart stroke volume is provided to a destination device.

18 Claims, 10 Drawing Sheets

(56) References Cited

U.S. PATENT DOCUMENTS

| | | | |
|---|---|---|---|
| 5,971,934 | A | 10/1999 | Scherer et al. |
| 6,004,274 | A | 12/1999 | Nolan et al. |
| 6,045,509 | A | 4/2000 | Caro et al. |
| 6,162,180 | A | 12/2000 | Miesel et al. |
| 6,186,955 | B1* | 2/2001 | Baura .................. 600/526 |
| 6,322,514 | B1 | 11/2001 | Holte |
| 6,390,977 | B1 | 5/2002 | Faithfull et al. |
| 6,582,656 | B1 | 6/2003 | Steuer et al. |
| 6,615,064 | B1 | 9/2003 | Aldrich |
| 6,681,128 | B2 | 1/2004 | Steuer et al. |
| 6,687,535 | B2* | 2/2004 | Hautala et al. .......... 600/520 |
| 6,709,402 | B2 | 3/2004 | Dekker et al. |
| 6,731,963 | B2 | 5/2004 | Finarov et al. |
| 6,757,554 | B2 | 6/2004 | Rubinstein et al. |
| 6,829,501 | B2 | 12/2004 | Nielsen et al. |
| 7,011,631 | B2 | 3/2006 | Davis et al. |
| 7,024,244 | B2 | 4/2006 | Muhlenberg et al. |
| 7,029,447 | B2 | 4/2006 | Rantala |
| 7,220,230 | B2 | 5/2007 | Roteliuk et al. |
| 7,226,418 | B2* | 6/2007 | Kim .................. A61B 5/022 600/485 |
| 7,422,562 | B2 | 9/2008 | Hatib et al. |
| 7,651,466 | B2 | 1/2010 | Hatib et al. |
| 2003/0013980 | A1 | 1/2003 | Starr et al. |
| 2003/0120164 | A1 | 6/2003 | Nielsen et al. |
| 2005/0004481 | A1* | 1/2005 | Xue et al. .................. 600/509 |
| 2006/0155661 | A1* | 7/2006 | Morgan .......... G06F 19/345 706/18 |
| 2008/0081961 | A1 | 4/2008 | Westbrook et al. |
| 2008/0269626 | A1 | 10/2008 | Gallagher et al. |
| 2010/0185084 | A1* | 7/2010 | Zhang .............. A61B 5/029 600/425 |
| 2010/0280396 | A1* | 11/2010 | Zhang .............. A61B 5/021 600/485 |
| 2012/0150003 | A1 | 6/2012 | Zhang |

OTHER PUBLICATIONS

Pier Guiseppe Agostoni, et al., "Non-invasive Measurement of Cardiac Output During Exercise by Inert Gas Rebreathing Technique: A New Tool for Heart Failure Evaluation", J Am Coll Cardiol, 2005, vol. 46, pp. 1779-1781.

Ron Dueck, "Noninvasive Cardiac Output Monitoring", Chest. 2001, vol. 120, pp. 339-341.

* cited by examiner

| Patient signals | Parameters and index | Functionality and relations for calculating CO/SV |
|---|---|---|
| ECG or other electrophysiological signals | Heart rate, HR | $CO = SV \times HR$ |
| | Amplitude of R wave, $A_R$ | Indirect index of cardiac function strength for estimation of the CO |
| | Time length of QT wave, $T_{QT}$ | Indirect index of cardiac function duration (systolic level) for estimation of the CO |
| | Other parameters from ECG signals | |
| Blood pressure signals (esp. the non-invasive pressure waveform) | Systolic-Diastolic pressures, $P_{SYS}$, $P_{DIA}$ | Direct parameters of blood pressure strength |
| | Mean blood pressure, $P_{Mean}$ | Direct parameters of blood pressure strength |
| | Pressure duration, $T_{pressure}$ | Direct parameters of blood pressure duration |
| | Systolic pressure cycle, $T_{Systolic}$ | Direct parameters of systolic blood pressure duration |
| | Other parameters from blood pressure signals | |
| SPO2 signals | Max SPO2 amplitude, $A_{P1}$ | Indirect index of cardiac function strength (oxygen level) for estimation of the CO |
| | Max-Min SPO2 amplitude, $A_{P1\_base}$ | Indirect index of cardiac function strength (oxygen level) for estimation of the CO |
| | $\Delta$ SPO2 amplitude, $A_{P1-P2}$ | Indirect index of cardiac function strength (oxygen content) for estimation of the CO |
| | Other parameters from SPO2 signals | |

FIGURE 3B

| Patient signals | Parameters and index | Functionality and relations for calculating CO/SV |
|---|---|---|
| Temperature signals | Averaging temperature, $T_{mean}$ | Indirect index of blood flow speed for estimation of the CO |
| | Max temperature, $T_{max}$ | Indirect index of blood flow speed for estimation of the CO |
| | Min temperature, $T_{min}$ | Indirect index of blood flow speed for estimation of the CO |
| | Other parameters from temperature signals | |
| Chest impedance | Averaging impedance, $R_{mean}$ | Indirect index of blood flow size and volume for estimation of the CO |
| | Max impedance, $R_{max}$ | Indirect index of blood flow size and volume for estimation of the CO |
| | Min impedance, $R_{min}$ | Indirect index of blood flow size and volume for estimation of the CO |
| | Other parameters from chest impedance signals | |

| Signal type | Potential derived parameters and calculation |
|---|---|
| ECG or other electrophysiological signals | Dominant frequency, $f_{ECG}$ |
| | ECG energy, $E_{ECG}$ |
| | ECG waveform entropy and ECG HOS index, $Entropy_{ECG}$ |
| | Other potential derived ECG related parameters |
| Blood pressure signals (esp. the non-invasive blood pressure waveform) | Blood pressure gradient, dP/dt |
| | Blood pressure energy, $E_{ECG}$ |
| | Blood pressure variation, standard deviation, |
| | Other derived parameters from blood pressure signals |
| SPO2 signals | SPO2 waveform energy, $E_{SPO2}$ |
| | SPO2 signal variation, standard deviation, |
| | Other parameters from SPO2 signals |
| Continuous temperature signals | Temperature standards deviation, variation, |
| | Other parameters from temperature signals |
| Continuous chest impedance signal | Impedance waveform integration energy, $E_{IMPE}$ |
| | Impedance standards deviation, variation, |
| | Other derived parameters from chest impedance signals |
| Other type patient signals | Other potential derived patient parameters |

FIGURE 9

SYSTEM FOR NON-INVASIVE CARDIAC OUTPUT DETERMINATION

This is a non-provisional application of provisional application Ser. No. 61/601,697 filed Feb. 22, 2012, by H. Zhang.

FIELD OF THE INVENTION

This invention concerns a system for determining cardiac output or stroke volume based on a weighted summation, over a particular time period, of values of a selected patient parameter.

BACKGROUND OF THE INVENTION

Heart stroke volume (SV) determination is used for patient health status monitoring, especially for patients in a CCU (critical care unit) and ICU (intensive care unit). However known clinical methods for measuring and monitoring cardiac output (CO) and SV are typically invasive, involving use of an intra-cardiac catheter and blood pressure based signal acquisition, for example. Known non-invasive and minimally invasive methods for CO/SV estimation, include impedance based methods and the use of angiographic images. But the known methods are usually not accurate or reliable, and need extensive expertise and clinical experience for accurate interpretation and appropriate cardiac rhythm management.

A cardiovascular system comprises components including, a pump (the heart), a carrier fluid (blood), a distribution system (arteries), an exchange system (capillary network), and a collecting system (venous system). Blood pressure is a driving force that propels blood along the distribution network. Stroke volume (SV) is the volume of blood pumped by the right and left ventricle of the heart in one contraction. Specifically, it is the volume of blood ejected from ventricles during systole. The stroke volume does not comprise all of the blood contained in the left ventricle. Normally, only about two-thirds of the blood in the ventricle is ejected with each beat. The blood actually pumped from the left ventricle comprises the stroke volume and it, together with the heart rate, determines the cardiac output (CO). Hemodynamic and cardiac output analysis, such as SV measurement improve analysis and characterization of cardiac pathology and disorders, and even enable prediction of occurrence of life-threatening events. Hence, accurate and precise hemodynamic measurement, parameter calculation, efficient diagnosis, and reliable evaluation are desired to monitor patient health status.

Accurate clinical assessment of circulatory status is particular desirable in critically ill patients in an ICU and patients undergoing cardiac, thoracic, or vascular interventions. As patient hemodynamic status may change rapidly, continuous monitoring of cardiac output provides information enabling rapid adjustment of therapy. CO/SV are important parameters used for cardiac/heart function characterization. Known methods for CO/SV determination include, Fick principle methods, Bio-impedance and conduction methods, Doppler ultrasound, arterial pulse and image contour analysis methods. However these methods have different kinds of limitation and burdens. Known clinical methods for CO/SV calculation are typically invasive, requiring catheters that add to clinical procedure complexity and present risk. Known clinical methods for cardiac output estimation are often complex and time consuming and are unsuited to some clinical environments or for a brief cardiac function check. Known methods for CO/SV estimation, such as indicator dilution techniques, Fick principle, Bio-impedance and conduction methods, use different kinds operating principles resulting in different kinds of data deviation and errors. These cardiac output calculation methods are sensitive to quality of sensor signals and may be unreliable in noisy environments. A system according to invention principles addresses these deficiencies and related problems

SUMMARY OF THE INVENTION

A system improves accuracy of determination of patient cardiac status using non-invasive monitoring involving different kinds of patient signals (e.g., ECG, blood pressure, SPO2) in calculating and characterizing cardiac output and stroke volume and deviation and related cardiac function parameters for diagnosing and quantifying patient health status. A method determines cardiac output or stroke volume. The method includes receiving signal data representing multiple parameters of a patient concurrently acquired over a particular time period and comprising at least one of, (a) a parameter derived from an ECG waveform of the patient, (b) a parameter derived from a blood pressure signal of the patient, (c) a parameter derived from signal data representing oxygen content of blood of the patient and (d) a parameter derived from a patient cardiac impedance value. The method uses a selected parameter of the multiple concurrently acquired parameters in calculating a heart stroke volume of the patient comprising volume of blood transferred through the blood vessel in a heart cycle, in response to, a combination of a weighted summation of values of the selected parameter over the particular time period. Data representing the calculated heart stroke volume is provided to a destination device.

DETAILED DESCRIPTION OF THE INVENTION

A system improves accuracy of determination of patient cardiac status using non-invasive monitoring involving different kinds of patient signals (ECG, blood pressure, SPO2, for example) and patient parameters in calculating and characterizing cardiac output and stroke volume. The non-invasive method is utilized to evaluate and characterize CO/SV and CO/SV deviation, and related cardiac function parameters for diagnosing and quantifying patient health status. The system quantitatively derives CO/SV based on hemodynamic and electrophysiological patient signals. Instead of using invasive (including least or minimal) blood pressure measurements, the system uses non-invasive blood pressure (NIBP) and SPO2 oximetric signal based determination of CO. SPO2 is typically used to measure blood oxygen in capillaries, and is advantageously used by the system to quantify and characterize patient health status and identify asthma severity and predict atrial fibrillation, for example. In an embodiment, a combination of NIBP, ECG, SPO2 (Oximetry data) is utilized to calculate cardiac output and stroke volume. The system provides a link between multiple patient signals and heart cardiac output. Non-invasive CO/SV determination and patient status determination is facilitated by function ratio determination between heart function and cardiac tissue status. SPO2 is a valuable vital sign used to monitor patient health status, by measuring the saturation of hemoglobin with oxygen using pulse Oximetry. Further, a link between a heart pump (CO/SV) and blood flow in small blood vessels (capillaries), is determined.

Figure 1:
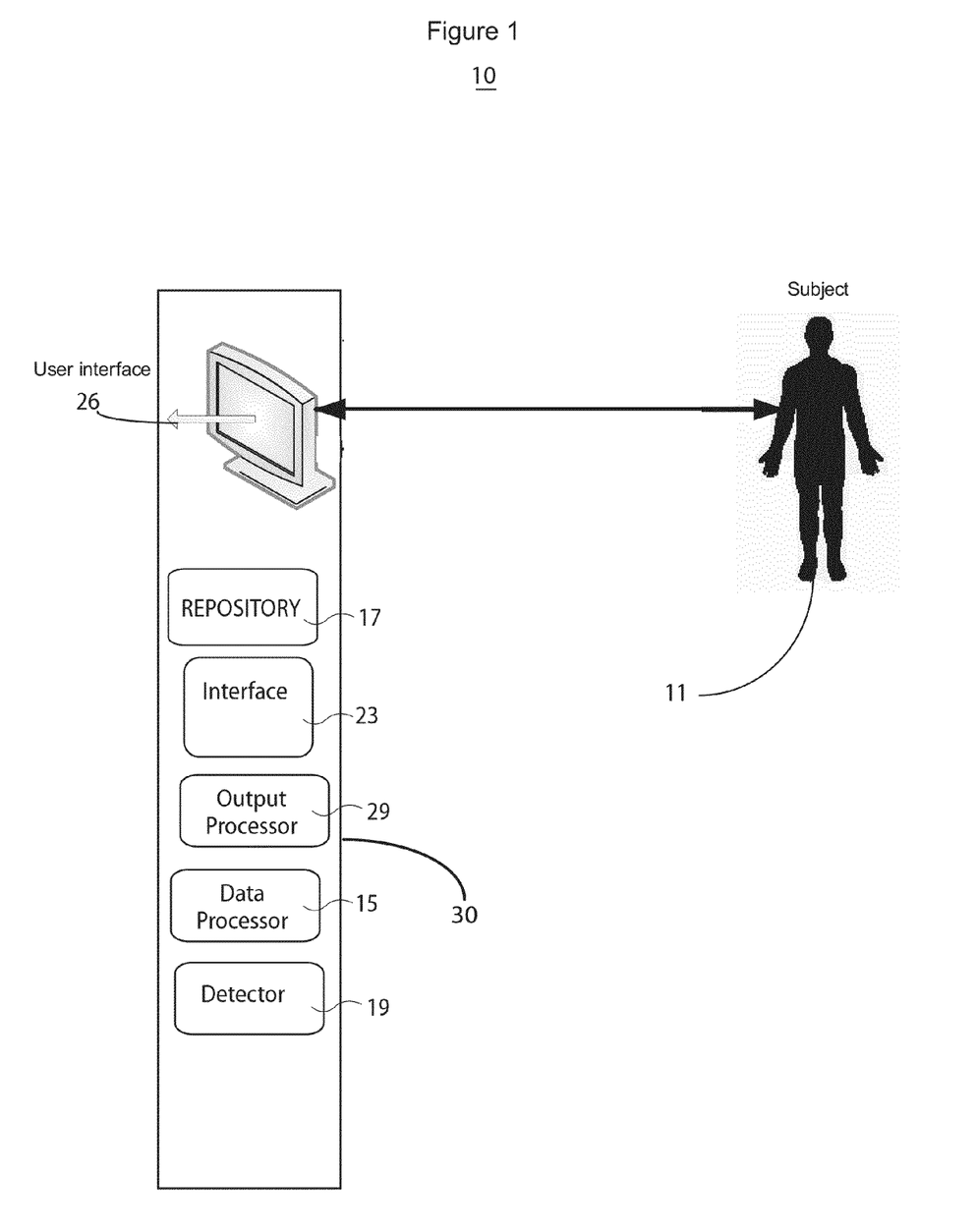
FIG. 1 shows a system for determining cardiac output or stroke volume, according to invention principles.

FIG. 1 shows system 10 for determining cardiac output or stroke volume. System 10 comprises at least one computer system, workstation, server or other processing device 30 including repository 17, data processor 15, interface 23, output processor 29, detector 19 and a user interface 26. Interface 23 comprising patient monitoring devices, receives signal data representing multiple parameters of a patient concurrently acquired from patient 11 over a particular time period and comprising parameters derived from an ECG waveform of the patient, parameters derived from a blood pressure signal of the patient, parameters derived from signal data representing oxygen content of blood of the patient and parameters derived from a patient cardiac impedance value. The signal data representing oxygen content of blood of the patient comprises a blood oxygen saturation (SPO2) signal representing oxygen content (e.g., SPO2 data) of blood in a patient vessel over multiple heart beat cycles. SPO2 signal waveform data is acquired by non-invasive sensors by using infrared light, such as Massimo, Nellcor, Nonin SPO2 acquisition sensors and systems. Data processor 15 uses a selected parameter of the multiple concurrently acquired parameters of a patient in calculating a heart stroke volume of the patient comprising volume of blood transferred through the blood vessel in a heart cycle, in response to, a combination of a weighted summation of values of the selected parameter over the particular time period. Output processor 29 provides data representing the calculated heart stroke volume to a destination device and stores the data in repository 17. Repository of data 17 stores received signal data and user interface 26 provides a display for presentation of alert messages and determined signal parameters. Detector 19 detects and characterizes cardiac arrhythmia using a calculated stroke volume.

Figure 2:
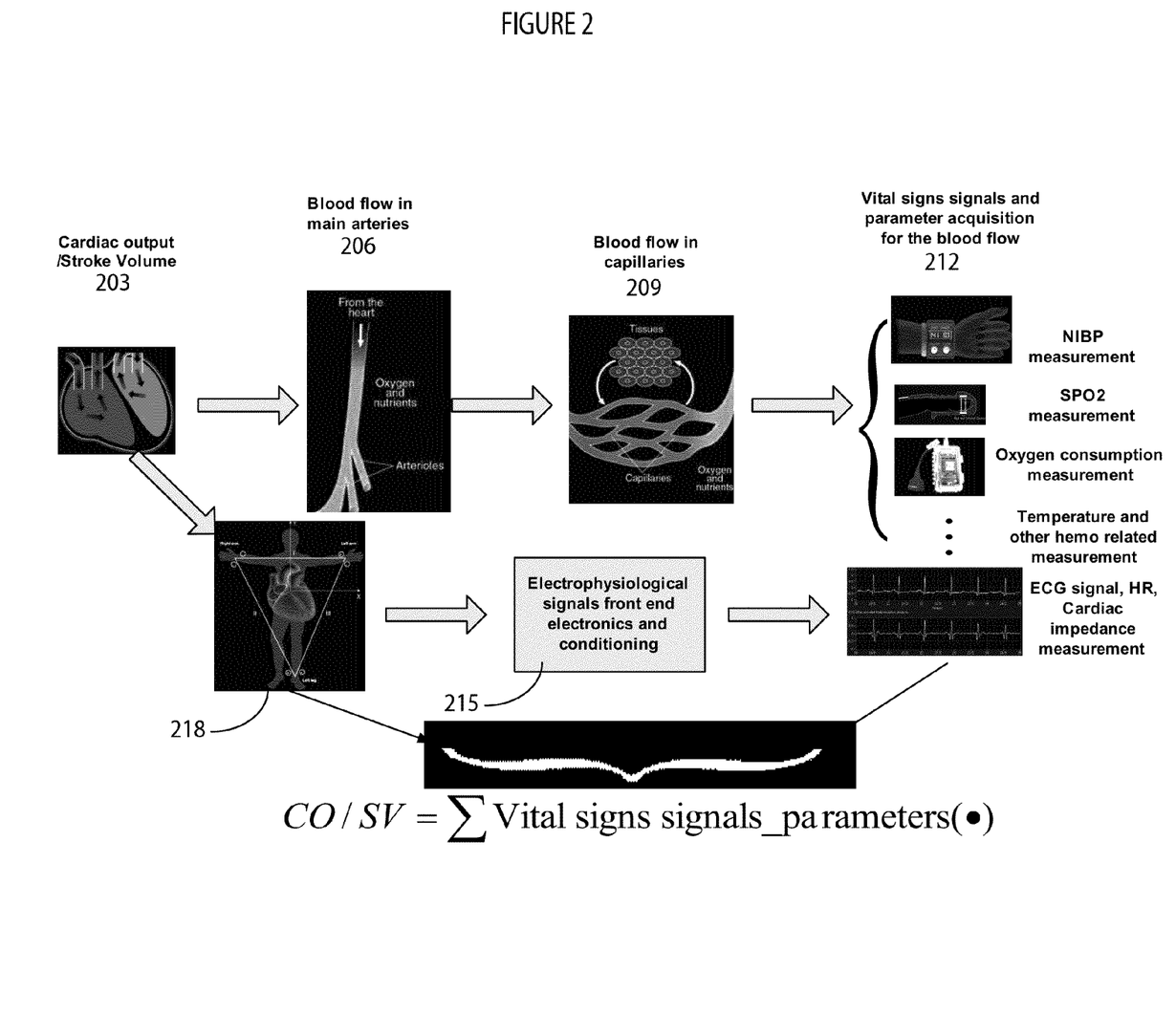
FIG. 2 shows patient vital sign acquisition and blood flow mapping from heart to body capillaries, according to invention principles.

FIG. 2 shows patient vital sign acquisition and blood flow mapping from heart to body capillaries. Typically a left ventricle 203 pumps blood into main arteries 206 which transport the blood to small blood vessels, organs, and eventually to body capillaries 209 and arm and finger tip 212. The finger tip is used for SPO2 oximetric parameter measurement and the arm is used for Non-invasive Blood Pressure (NIBP) measurement. In addition oral oxygen volume consumption is measured and ECG signals 218 are acquired with attached leads for chest impedance vector determination and the ECG signals are processed by unit 215. In the vital sign signal parameter measurements, a parameter may have a relationship (linear or nonlinear) with cardiac blood output. For example, NIBP shows blood pressure which can be used to determine a workflow and speed. SPO2 shows Oxygen content which is used to associate an average volume and size of blood flow. Oxygen consumption via mouth is used to associate real time blood flow volume rate from a heart. ECG and impedance are used to estimate chest volume and blood flow size. In one embodiment, body temperature and heart rate may also be used for determining cardiac output.

Multiple parameters (which relate to blood flow) are advantageously integrated and combined by data processor 15 for calculation of CO and SV. It is not necessary to use all the parameters to obtain CO however the more parameter used in the calculation, the more accurate is the CO determination. Data processor 15 uses multiple patient parameters for CO determination in an embodiment employing an equation, $$\frac{CO}{SV} = \sum \text{Vital signs signals\_parameters}(\bullet)$$
$$= \sum_{i \in ROI\_paramters\_number} \alpha_i(t) \cdot f_i(t)$$

In which, Vital signs signals_parameters is a function for calculating indices based on vital sign and patient signal parameters, ROI_paramters_number represents a set of integers ranging from 1 to the total number of vital sign and patient signal parameters, $\alpha_i(t)$ represents a weighting coefficient which determines relative contribution from a particular vital sign parameter; $f_i(t)$ represents vital sign and patient signal parameters, such as mean blood pressure, systolic blood pressure, SPO2 saturation level, (t) represents time and the coefficient and patient signals may be time varying (however for the same patient and context, the coefficients and patient signals may be stable).

Figure 3A:
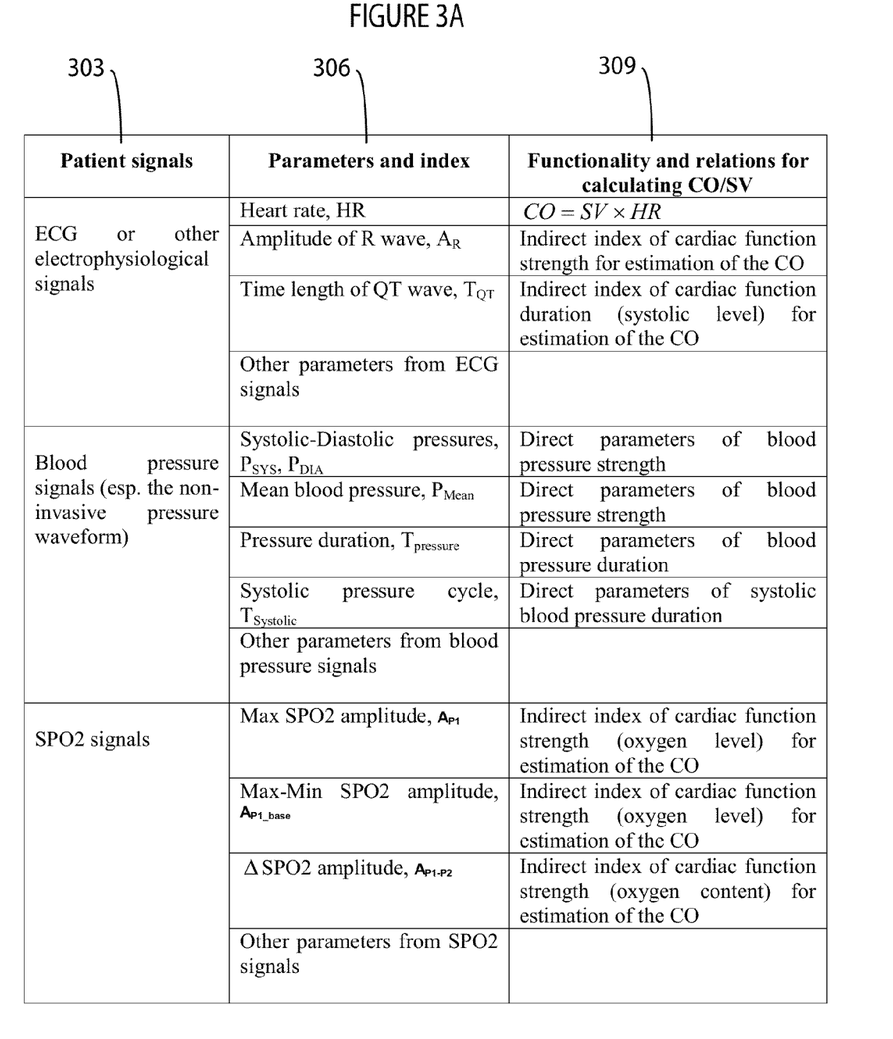
FIGS. 3A and 3B show a Table of patient signals and parameters advantageously utilized in calculation of CO/SV, according to invention principles.
Figure 3B:
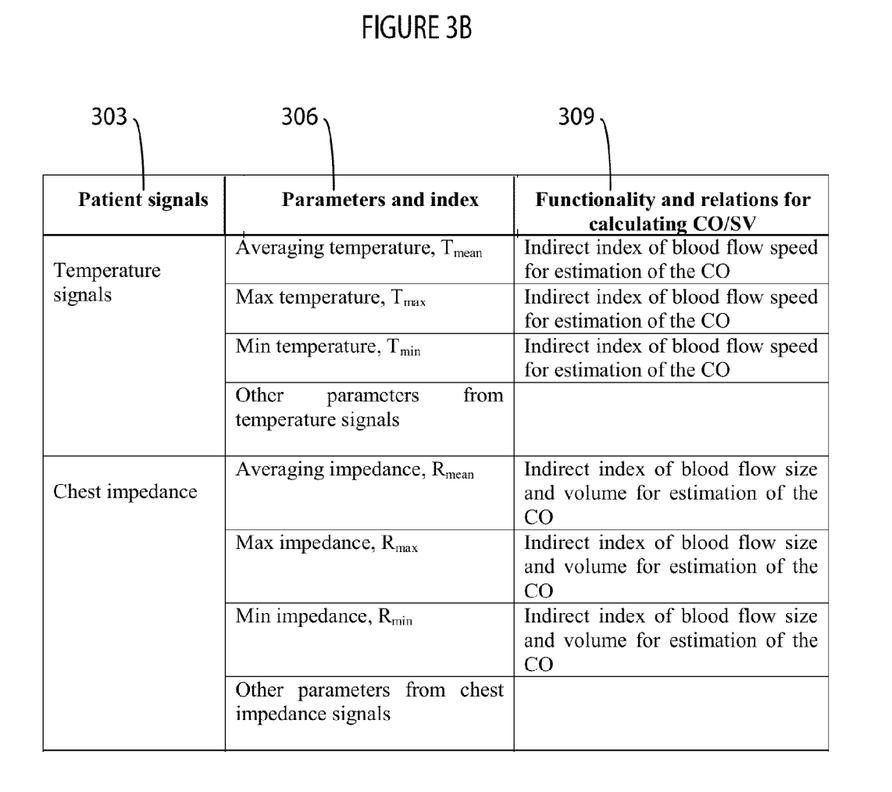

FIGS. 3A and 3B show a Table of patient signals and parameters advantageously utilized in calculation of CO/SV. System 10 (or in another embodiment a user) adaptively dynamically selects different vital sign signals and related parameters for use in CO determination in response to data identifying a clinical procedure being performed. Additionally, these coefficients may be different in different situations, such as when a patient is at rest or exercising. However coefficients may be similar in corresponding situations at different times. In this section, parameters $f_i(t)$ comprise direct patient signal parameter measurement values. Patient signals including ECG, blood pressure, SPO2, temperature and impedance signals are shown in column 303 with corresponding parameters identified in column 306 and corresponding determined functions in column 309 which are used to calculate patient heart cardiac output or stroke volume. Data processor 15 calculates cardiac output using a sample time window size (5-10 heart beat cycles in one embodiment) selected for averaging and variation determination. The sample time window size is determined by data processor 15 automatically and adaptively according to noise level and a type of clinical procedure being performed.

In one embodiment, data processor 15 uses patient signals and measured parameters in CO/SV calculation using, $$CO/SV =$$
$$\sum_{i \in ROI\_paramters\_number} \alpha_i(t) \cdot f_i(t) = \left( \sum_{i \in ECG} \alpha_{ECG}(i) \cdot \text{ECG\_parameters}(i) + \right.$$

$$-\text{continued}$$
$$\sum_{j \in SPO2} \alpha_{SPO2}(j) \cdot SPO2\_parameters(j) +$$
$$\sum_{m \in NIBP} \alpha_{NIBP}(m) \cdot IBP\_parameters(m) +$$
$$\sum_{n \in TEMP} \alpha_{TEMP}(n) \cdot TEMP\_parameters(n) +$$
$$\sum_{p \in IMPE} \alpha_{IMPE}(p) \cdot IMPE\_parameters(p) + \ldots \Bigg) \Big/ W$$

where, W is number of types of vital sign signals (if two types of patient signals e.g. ECG and SPO2 signals are utilized in calculation of CO, W is 2). Different vital sign signal parameters are combined with different coefficients. These coefficients are adaptively updated by data processor 15 based on patient status, such as heart rhythm, drug delivery and exercise status.

In particular situations, a simplified function is used for CO/SV calculation. Specifically, where for example, ECG, NIBP, impedance signals are not available, CO is determined from continuous SPO2 and patient temperature measurements using, $$CO/SV = \Bigg(\sum_{j \in SPO2} \alpha_{SPO2}(j) \cdot SPO2\_parameters(j) +$$
$$\sum_{n \in TEMP} \alpha_{TEMP}(n) \cdot TEMP\_parameters(n)\Bigg) \Big/ 2$$

According to the reliability, sensitivity and accuracy requirements, single or multiple parameters may be used from each type of patient signal. For example, Δ SPO2 amplitude $A_{P1-P2}$ (peak to peak SPO2 signal amplitude) and average body temperature, $T_{mean}$ are used for CO estimation with corresponding coefficients, $$\alpha_{SPO2}=2.75 \text{ and } \alpha_{TEMP}=0.15;$$

$$CO=(2.75*A_{P1-P2}+0.15*T_{mean})/2$$

Figure 4:
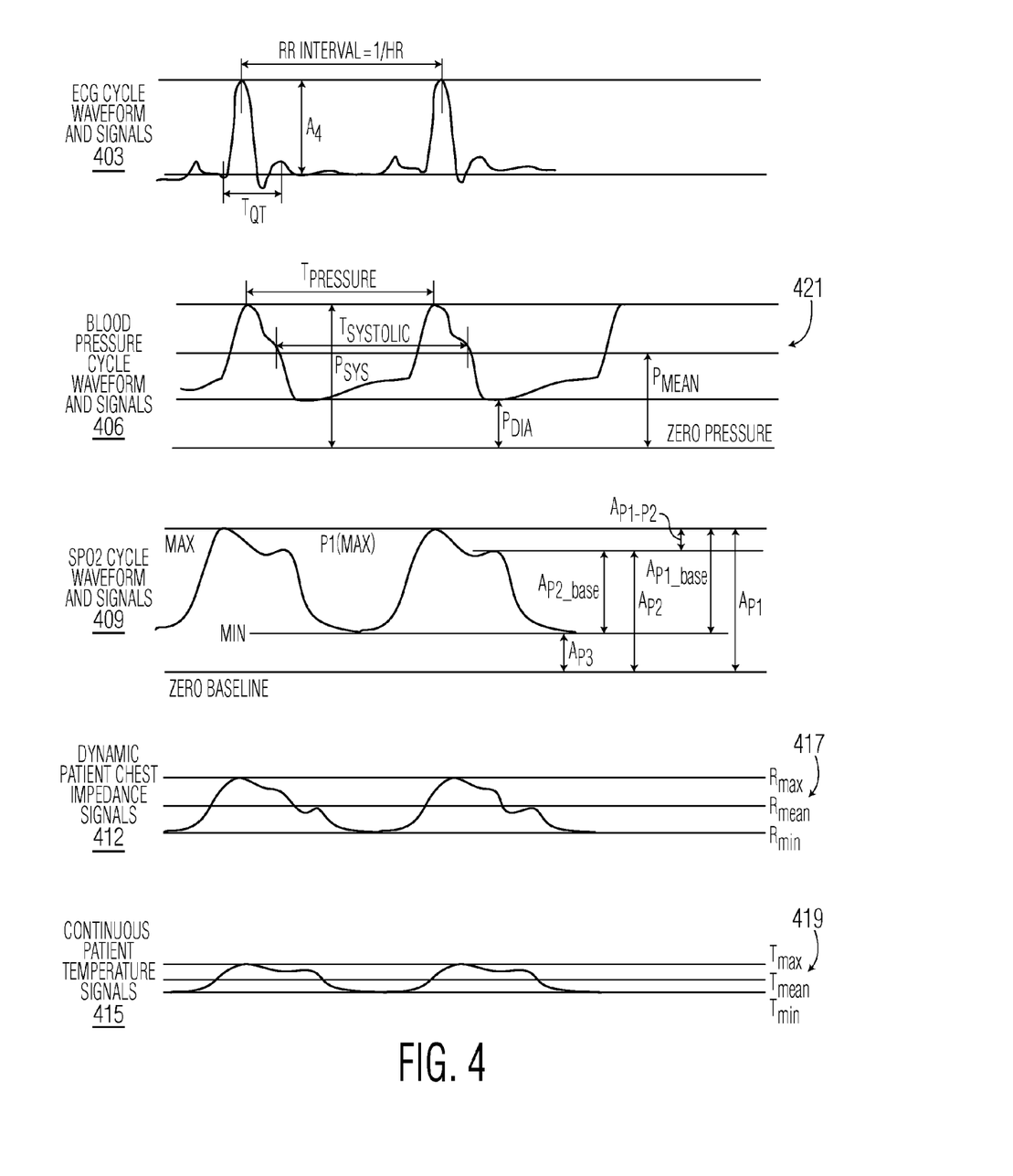
FIG. 4 shows different patient signals and measurements used for cardiac output and stroke volume calculation, according to invention principles.

FIG. 4 shows different patient signals and measurements used for cardiac output and stroke volume calculation. Different kinds of patient may use selected signals of, an ECG signal 403, non-invasive blood pressure 406, SPO2 signal amplitude 409, impedance signal 412 and temperature signal 415 as described in the table of FIGS. 3A and 3B, for CO determination. CO is calculated in one embodiment using parameters such as heart rate, non-invasive blood pressure amplitude, SPO2 amplitude, dynamic patient chest impedance, average (mean) temperature values. The average impedance value 417, average temperature value 419 and average blood pressure value 421 are averaged over multiple cardiac cycles decreasing impact of noise and CO calculation variation.

Figure 5:
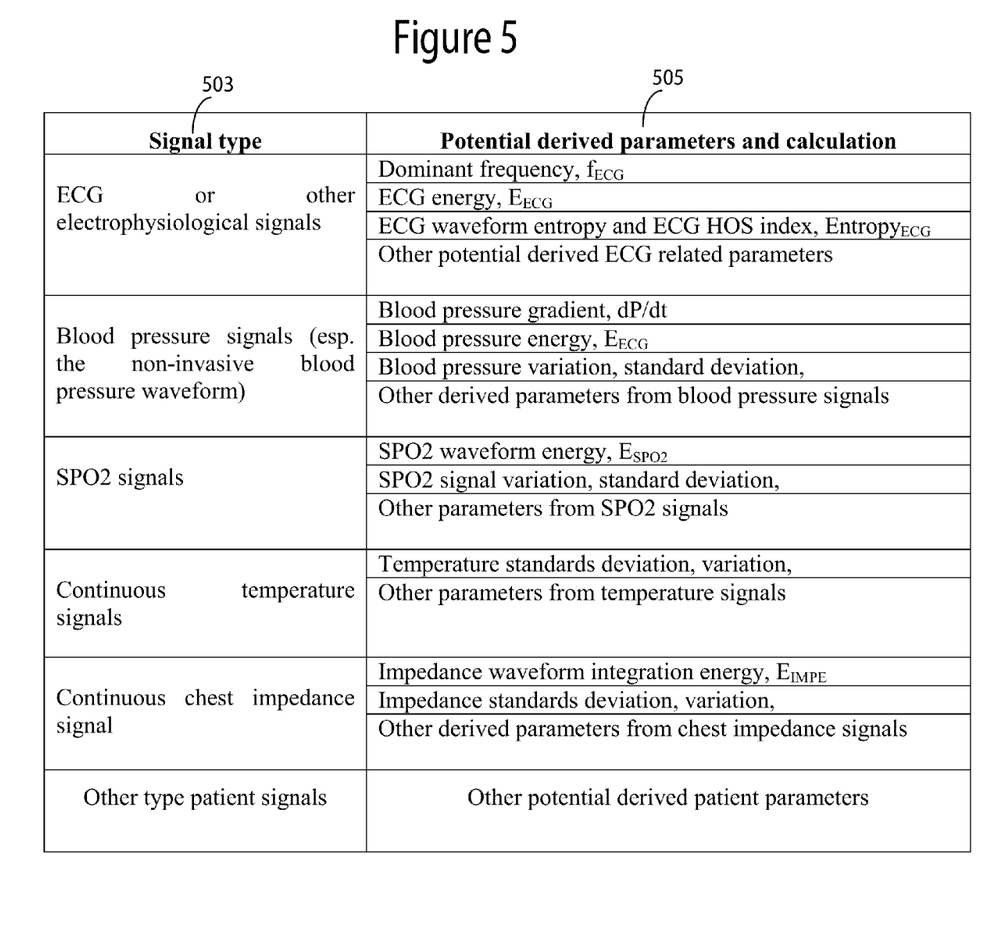
FIG. 5 shows a Table of derived patient parameters used for CO and SV calculation, according to invention principles.

FIG. 5 shows a Table of derived patient parameters used for CO and SV calculation. Signal type is indicated in column 503 with corresponding derived parameters in column 505. In one embodiment, CO and SV are calculated by combining direct patient signal measurement parameters and derived parameters. The patient signals and parameter measurements include rate of pressure change Dp/dt, signal variance, variation, high order statistics (HOS), frequency, energy, entropy and spectrum. In one embodiment, CO and SV are calculated by combining direct patient signal measurement parameters and indirect derived parameters as follows, $$CO/SV = \delta_1 \cdot \Big[\sum \text{Vital signs signals\_parameters}(\bullet)\Big] +$$
$$\delta_2 \cdot \Big[\sum \text{Derived patient signals\_index}(\bullet)\Big]$$
$$= \delta_1 \cdot \Bigg[\sum_{i \in ROI\_paramters\_number} \alpha_i(t) \cdot f_i(t)\Bigg] +$$
$$\delta_2 \cdot \Bigg[\sum_{j \in ROI\_index\_number} \beta_j(t) \cdot d_j(t)\Bigg]$$

where, $\delta_1$ and $\delta_2$ are a contribution ratio (weighting coefficient) used to calculate CO/SV from direct and indirect patient signals, ROI_index_number represents patient indirect derived parameters, such as energy, entropy, standard deviation, signal variation, $\alpha_i(t)$ and $\beta_j(t)$ are weighting coefficients for these patient signals and derived parameters. The parameters are adaptively automatically updated based on type of clinical procedure being performed and patient status (including the signal quality, noise level, signal acquisition position).

Patient demographic and clinical status factors, such as weight, height, gender, drug/medicine effects and treatment, are used to estimate cardiac output and stroke volume. These factors are summarized into coefficient λ in the CO/SV calculation function, (Function 1):

$$CO/SV = \lambda \cdot \begin{Bmatrix} S_1 \cdot \Big[\sum \text{Vital signs signals\_parameters}(\bullet)\Big] + \\ \delta_2 \cdot \Big[\sum \text{Derived patient signals\_index}(\bullet)\Big] \end{Bmatrix}$$
$$= \lambda \cdot \begin{Bmatrix} S_1 \cdot \Big[\sum_{i \in ROI\_paramters\_number} \alpha_i(t) \cdot f_i(t)\Big] + \\ \delta_2 \cdot \Big[\sum_{j \in ROI\_index\_number} \beta_j(t) \cdot d_j(t)\Big] \end{Bmatrix}$$

Different parameters are linearly or non-linearly combined and integrated and one of multiple different methods is selected to derive coefficients and ratios used for calculating cardiac output, such as an artificial neural network (ANN) or fuzzy algorithm.

Figure 6:
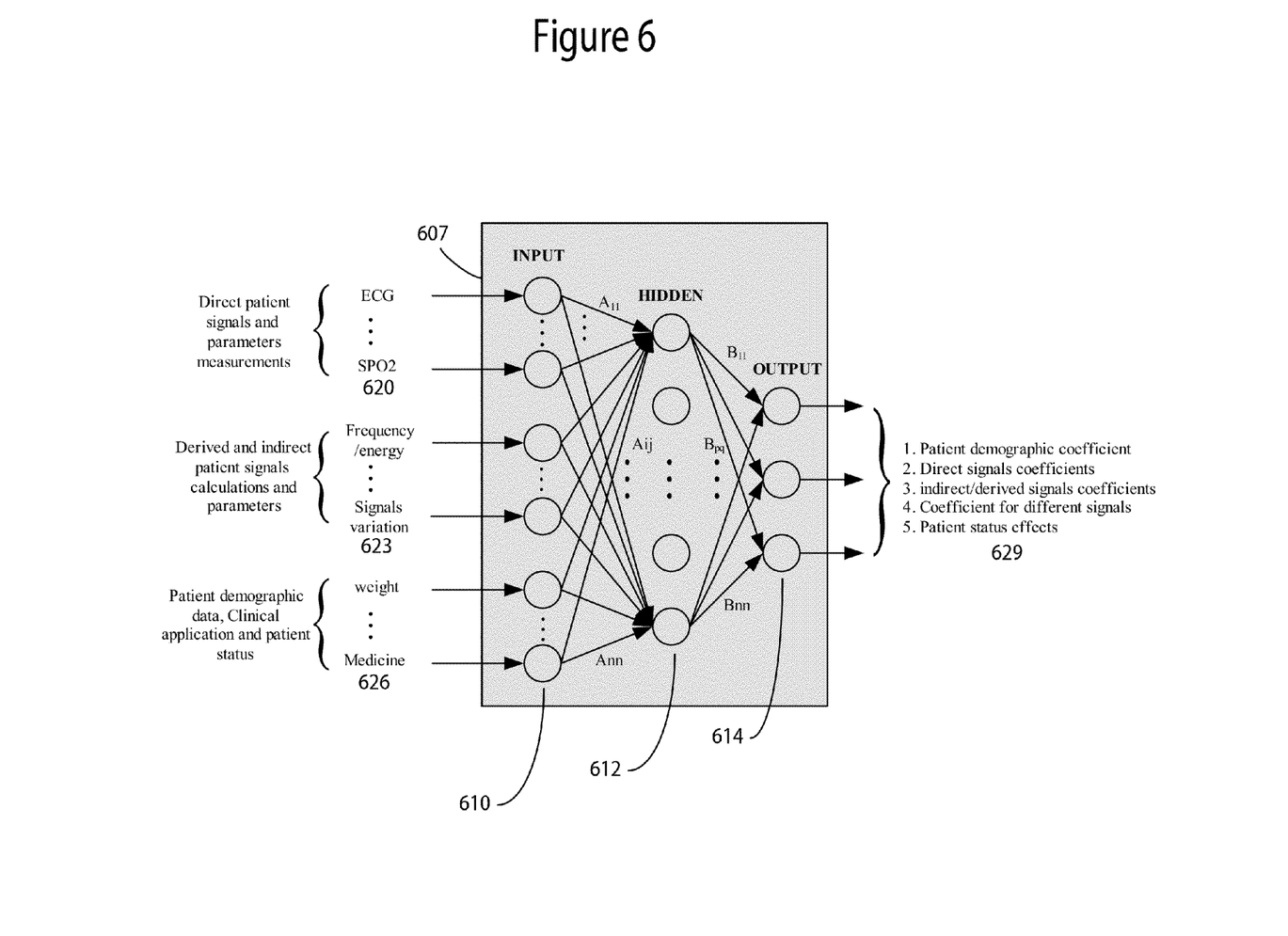
FIG. 6 shows an artificial neural network (ANN) for coefficient and weight determination and cardiac output calculation, according to invention principles.

FIG. 6 shows an artificial neural network (ANN) for coefficient and weight determination and cardiac output calculation. ANN unit 607 integrates and nonlinearly combines multiple kinds of patient information since different types of patient data and data patterns have a nonlinear relationship. ANN unit 607 comprises a three layer architecture for combining and integrating different kinds of parameters. including, heart rate, non-invasive blood pressure amplitude, SPO2 amplitude, dynamic patient chest impedance and temperature values 620 and associated derived parameters including frequency, energy and variation parameters 623 and weights, coefficients and patient demographic parameters 626. ANN unit 607 combines and maps parameters 620, 623 and 626, to output parameters 629. The output parameters 629 indicate patient demographic coefficients, direct signal coefficients, coefficients of derived parameters and patient status characteristics.

ANN unit 607 structure comprises 3 layers, an input layer 610, hidden layer 612 and output layer 614. ANN unit $A_{ij}$ weights are applied between input layer 610 and hidden layer 612 components of the ANN computation and $B_{pq}$ weights are applied between hidden layer 612 and calculation components 614 of the ANN computation. The $A_{ij}$ weights and $B_{pq}$ weights are adaptively adjusted and tuned using a training data set. ANN unit 607 incorporates a self-learning function that processes signals 620, 623 and 626 to increase the accuracy of calculated results using repository 17 of patient data. Repository 17 includes patient data comprising CO values acquired for patients of different demographic characteristics in different kinds of situations (such as rest, exercise). The patient data is used to train ANN unit 607 to provide real time coefficients for different patient signals, such as SPO2 amplitude, heart rate. ANN unit 607 has self-learning ability with accumulated data which increases the accuracy of calculated results. Thereby the coefficients and weights are adaptively and automatically updated in a real time calculation of cardiac output and stroke volume.

Figure 7:
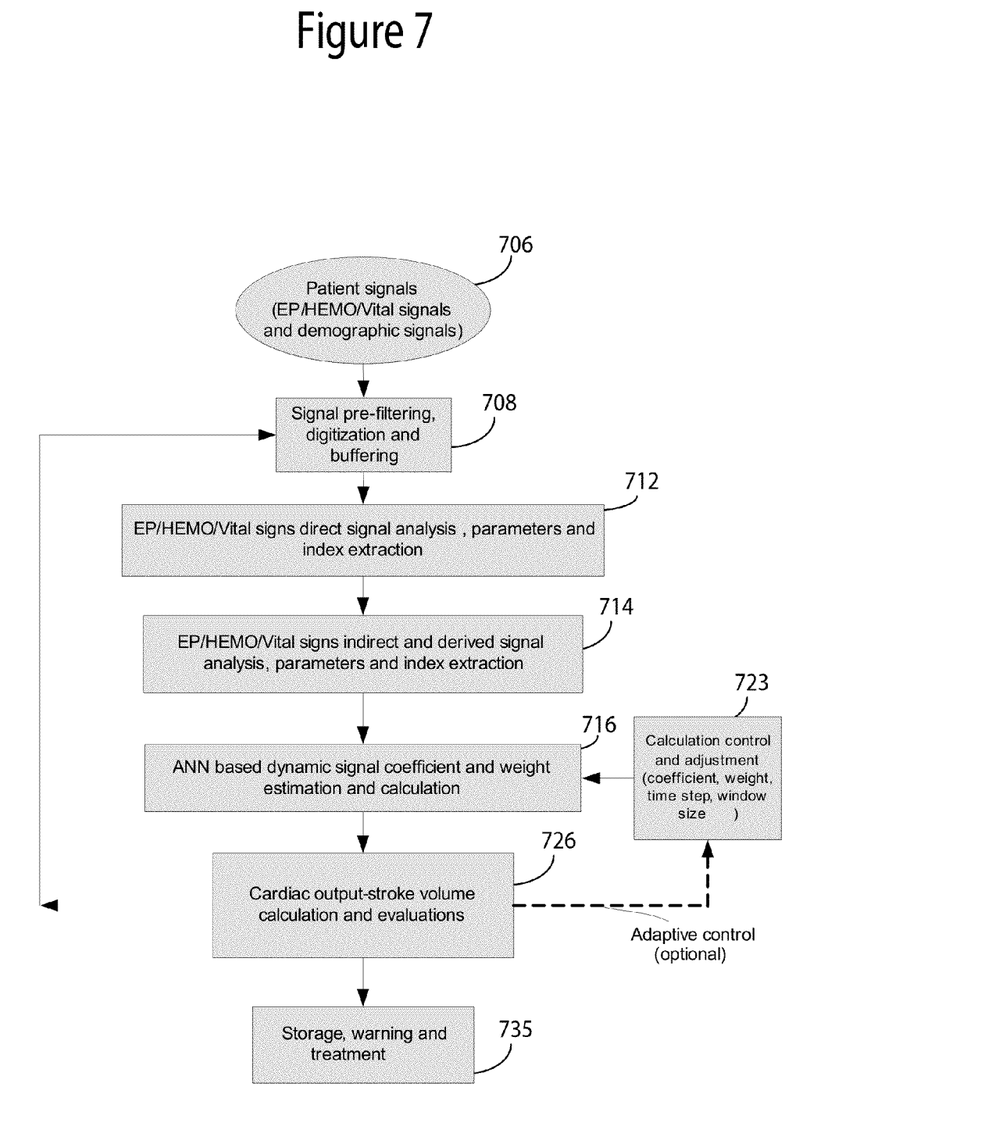
FIG. 7 shows a flowchart of a process for monitoring and characterizing cardiac output and stroke volume, according to invention principles.

FIG. 7 shows a flowchart of a process performed by system 10 (FIG. 1) for monitoring and characterizing cardiac output and stroke volume. Interface 23 buffers and digitizes a non-invasive blood pressure amplitude signal, blood oxygen saturation (SPO2) signal, an ECG signal and processes a heart rate signal, dynamic patient chest impedance data, temperature signal and other vital sign signals in step 708 received in step 706. Interface 23 in step 708 filters the received signal data using a filter adaptively selected in response to data indicating clinical application to remove patient movement and respiratory artifacts as well as power line noise. In step 712, processor 15 performs signal analysis involving heart cycle detection and signal segmentation into predetermined sections within a heart cycle and performs morphology analysis to identify peak values (maxima) and minimum values. Data processor 15 performs continuous real time SPO2 oximetric signal analysis and related calculations including determination of waveform parameters including signal maxima, peaks, minima, valleys and synchronized signal time durations, to derive the parameters of the Table of FIGS. 3A and 3B.

Data processor 15 detects peaks of waveforms within the received sampled data by synchronization with a heart electrical activity waveform and performs peak detection using a known peak detector and by identifying peaks of signals (e.g. ECG, SPO2, blood pressure signals) by segmenting a signal represented by sampled data into windows where the waves are expected and by identifying the peaks within the windows. An ECG signal is segmented into predetermined sections including Q, R, S, T, U wave segments within a heart cycle. The start point of a wave, for example, is identified by a variety of known different methods. In one method a wave start point comprises where the signal crosses a baseline of the signal (in a predetermined wave window, for example). Alternatively, a wave start point may comprise a peak or valley of signal. The baseline of the signal may comprise a zero voltage line if a static (DC) voltage signal component is filtered out from the signal. The signal processor includes a timing detector for determining time duration between the signal peaks and valleys. The time detector uses a clock counter for counting a clock between the peak and valley points and the counting is initiated and terminated in response to the detected peak and valley characteristics.

In step 714, processor 15 analyzes the received signal data and determined parameters including amplitudes and durations, to derive the indirect patient signal parameters of the Table of FIG. 5 including frequency, energy and statistical derived parameters. An ANN unit in processor 15 in step 716 performs signal coefficient estimation and calculation, such as to determine $\lambda$, $\alpha_i(t)$, $\beta_j(t)$ of the equation described in connection with FIG. 5 in one embodiment. These coefficients may be time varying or dependent on a patient situation and are adaptively and automatically updated in a real time mode to facilitate accurate CO calculation.

Data processor 15 in step 726 calculates cardiac output and stroke volume and updates the calculation by iteratively repeating the process from step 708 in response to receiving new input data over one or more heart cycles. Processor 15 in step 735 provides data representing the calculated heart stroke volume to a destination device, generates an alert message identifying an abnormality and communicates the message to a user and stores data indicating the heart stroke volume in repository 17. Processor 15 in step 723 adaptively adjusts a time window, window shift step, the number of samples in a calculation window used for calculation and adjusts the selected portions and ROI of a filtered signal and adjusts a threshold employed by processor 15 to improve abnormality detection.

Figure 8:
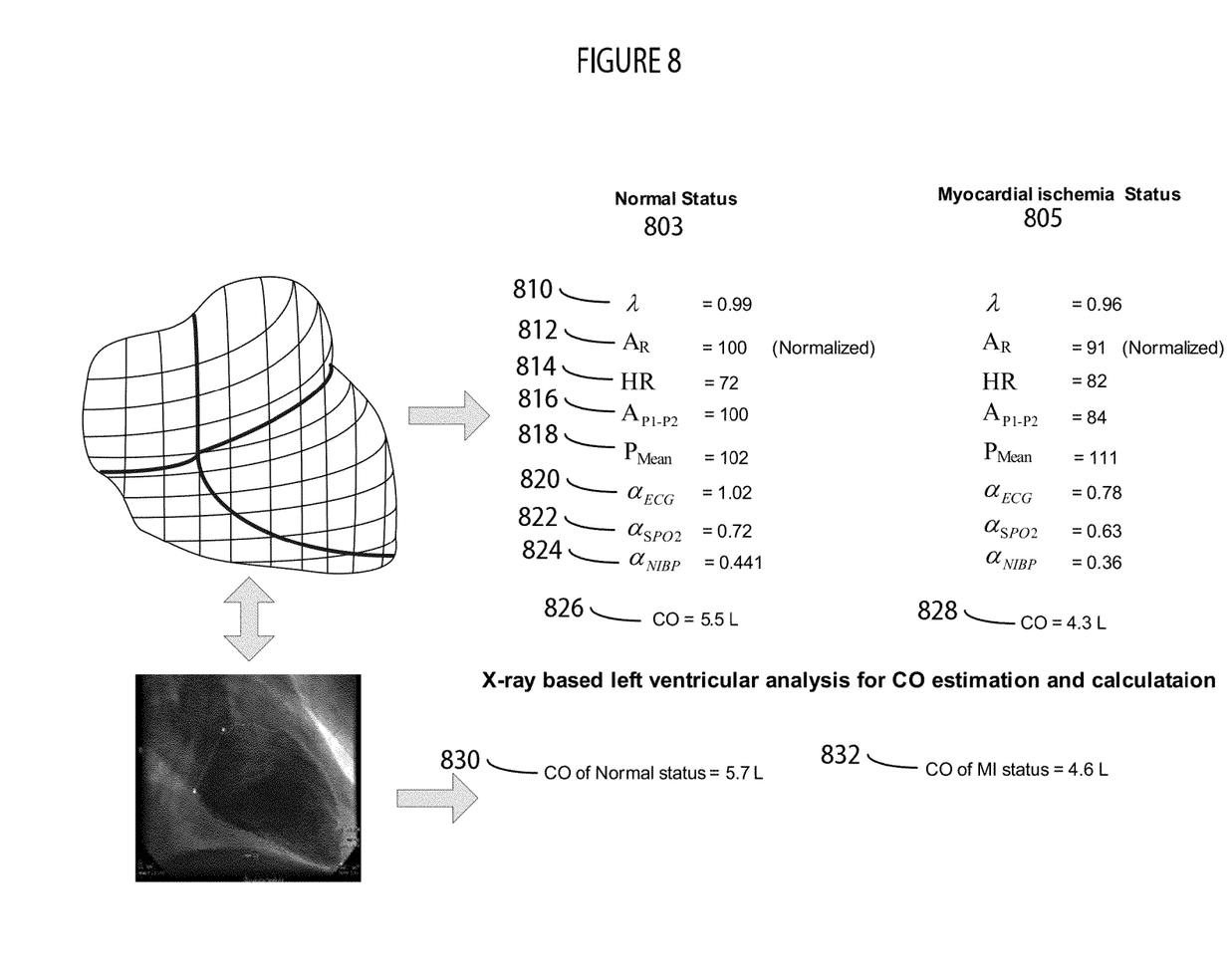
FIG. 8 shows comparison of calculated cardiac output for normal and myocardial ischemia conditions, according to invention principles, with a known X-ray image based cardiac output calculations.

FIG. 8 shows comparison of simulated calculated cardiac output of a patient in a normal health condition 803 and with a myocardial ischemia condition 805, according to invention principles and also with known X-ray image based cardiac output calculations. Function 1 described in connection with FIG. 5 is calculated in conditions 803, 805 using patient parameters including, R wave amplitude 812 in an ECG waveform, heart rate (HR) 814 derived from ECG signal analysis, $A_{P1-P2}$, peak to peak SPO2 amplitude 816 in an SPO2 waveform and Mean blood pressure, $P_{Mean}$ 818 in a non-invasive blood pressure measurement. For patient conditions 803, 805 six heart cycles are employed for mean value calculation, such as $A_R$, HR(=1/RR wave length). So in this example, the CO/SV calculation is, $$CO = \lambda \cdot \left[ \sum_{i \in ROI\_parameters\_number} \alpha_i(t) \cdot f_i(t) \right]$$
$$= \lambda \cdot [\alpha_{ECG} \cdot A_R + \alpha_{SPO2} \cdot A_{P1-P2} + \alpha_{NIBP} \cdot P_{mean}] * HR/3$$

In normal cardiac functional condition 803, averaged patient signal parameters are, $A_R$=100 (normalized value as reference) 812, HR=72 bpm 814, $A_{P1-P2}$=100 (normalized value as reference) 816, $P_{mean}$=102 mmHg 818. ANN unit 607 in response to training data, determines coefficients $\lambda$=0.99 810, $\alpha_{ECG}$=1.02 820, $\alpha_{SPO2}$=0.72 822 and $\alpha_{NIBP}$=0.441 824, respectively. Similarly, the corresponding patient signals and coefficients in myocardial ischemia condition 805 are $A_R$=91 812, HR=82 bpm 814, $A_{P1-P2}$=84 816, $P_{mean}$=111 mmHg 818, $\lambda$=0.96 810, $\alpha_{ECG}$=0.78 820, $\alpha_{SPO2}$=0.63 822, $\alpha_{NIBP}$=0.36 824. By comparison, it can be seen, during myocardial ischemia (compared with normal cardiac status), the heart rate is higher and blood pressure is higher while the R wave in the ECG signal and peak to peak SPO2 amplitude are lower. Based on the CO/SV equation, the cardiac output in normal cardiac condition is 5.5 L 826 and the cardiac output in MI condition is 4.3 L 828. Further, X-Ray image based left ventricular output calculation shows normal cardiac condition CO=5.7 L 830 and during the MI status, CO=4.6 L 832. Hence the results of this simulation show improved non-invasive patient signal based cardiac output calculation.

Figure 9:
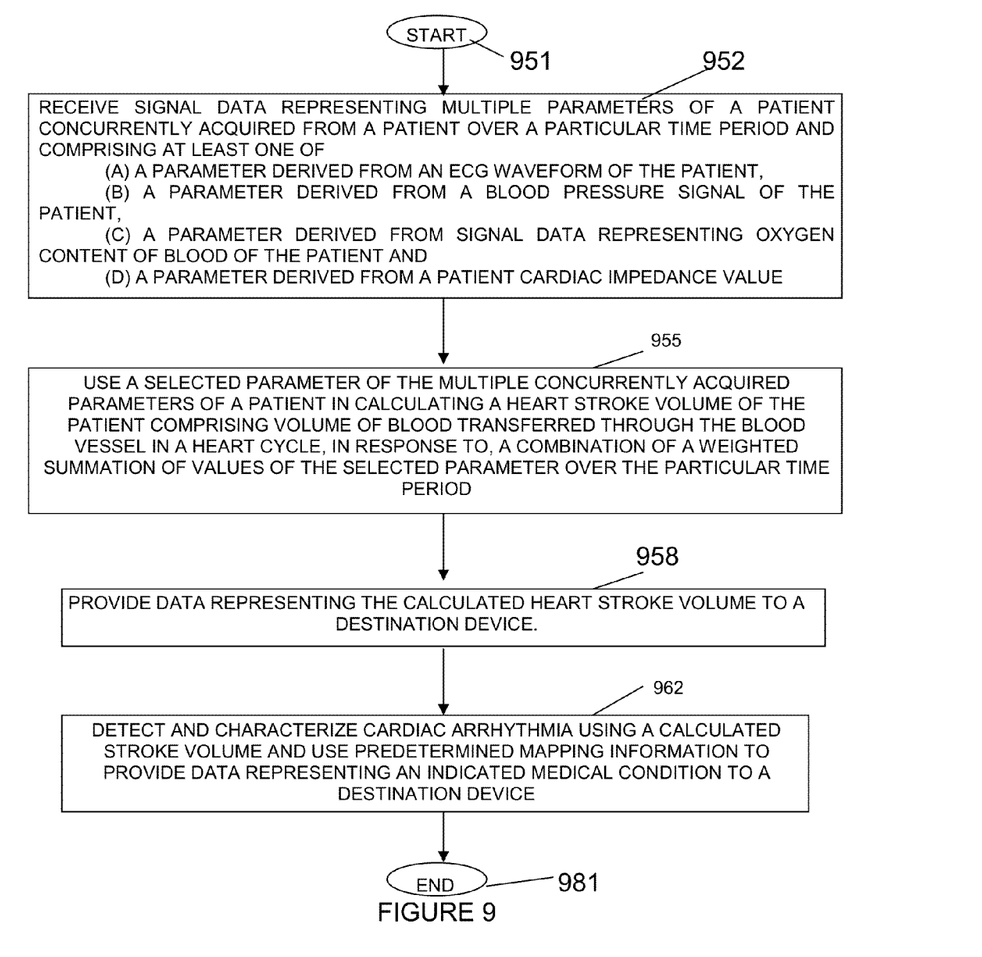
FIG. 9 shows a flowchart of a process used by a system for determining cardiac output or stroke volume, according to invention principles.

FIG. 9 shows a flowchart of a process used by system 10 (FIG. 1) for determining cardiac output or stroke volume. In step 952 following the start at step 951, interface 23 receives signal data representing multiple parameters of a patient. The multiple parameters are concurrently acquired from a patient over a particular time period and comprise at least one of, (a) a parameter derived from an ECG waveform of the patient, (b) a parameter derived from a blood pressure signal of the patient, (c) a parameter derived from signal data representing oxygen content of blood of the patient (a blood oxygen saturation (SPO2) signal, for example), (d) a parameter derived from a patient cardiac impedance value, (e) temperature of the patient, (f) invasive blood pressure of the patient, (g) non-invasive blood pressure of the patient and (h) a rate of change of blood pressure of the patient.

In step 955 data processor 15 uses a selected parameter of the multiple concurrently acquired parameters of a patient in calculating a heart stroke volume of the patient comprising volume of blood transferred through the blood vessel in a heart cycle, in response to, a combination of a weighted summation of values of the selected parameter over the particular time period. In another embodiment, processor 15 uses multiple concurrently acquired different parameters of a patient in calculating a heart stroke volume of the patient, in response to, a combination of a weighted summation of values of a first parameter and a weighted summation of values of a different second parameter, the summation being over the particular time period.

Processor 15 calculates a heart stroke volume of the patient using a weighted combination of at least two of, (a) a mean value of the selected parameter, (b) a maximum value of the selected parameter, (c) a minimum value of the selected parameter and (d) a variance of values of the selected parameter. Processor 15 in one embodiment, calculates a heart stroke volume of the patient using a weighted combination of one or more parameters and a function of the form, $$CO/SV = \sum \text{Vital signs signals\_parameters}(\bullet)$$
$$= \sum_{i \in ROI\_paramters\_number} \alpha_i(t) \cdot f_i(t)$$

where, $\alpha_i(t)$ represents a weighting coefficient which determines relative contribution from a particular patient parameter; $f_i(t)$ represents patient parameters and (t) represents time. Processor 15 further calculates a heart stroke volume of the patient in response to a factor representing reduction in blood flow volume from a patient heart to a particular anatomical location. In one embodiment processor 15 uses an artificial neural network configured using a training data set comprising data for the patient concerned. The neural network processes demographic data of the patient comprising at least two of, age, height, weight, gender and pregnancy status and processes the multiple parameters, in calculating a heart stroke volume of the patient.

Output processor 29 in step 958 provides data representing the calculated heart stroke volume to a destination device. In step 962, detector 19 detects and characterizes cardiac arrhythmia using a calculated stroke volume. Further, processor 15 uses predetermined mapping information associating ranges of calculated stroke volume or values derived from the calculated stroke volume with medical conditions and with particular patient demographic characteristics and with corresponding medical conditions. Processor 15 maps the calculated stroke volume to data indicating a medical condition of the patient and provides data representing the indicated medical condition to a destination device. Processor 15 uses patient demographic data including at least one of, age, weight, gender and height in comparing the calculated stroke volume with the ranges and generates an alert message indicating a potential medical condition. The process of FIG. 9 terminates at step 981.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. Computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s). A user interface processor or generator is a known element comprising electronic circuitry or software or a combination of both for generating display elements or portions thereof. A user interface comprises one or more display elements enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A graphical user interface (GUI), as used herein, comprises one or more display elements, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the elements for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display elements in response to signals received from the input devices. In this way, the user interacts with the display elements using the input devices, enabling user interaction with the processor or other device. The functions and process steps herein may be performed automatically or wholly or partially in response to user command. An activity (including a step) performed automatically is performed in response to executable instruction or device operation without user direct initiation of the activity. A histogram of an image is a graph that plots the number of pixels (on the y-axis herein) in the image having a specific intensity value (on the x-axis herein) against the range of available intensity values. The resultant curve is useful in evaluating image content and can be used to process the image for improved display (e.g. enhancing contrast).

The system and processes of FIGS. 1-9 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system quantitatively derives CO/SV based on hemodynamic and electrophysiological patient signals to quantify and characterize patient health status and identify asthma severity and predict atrial fibrillation, for example. Further, the processes and applications may, in alternative embodiments, be located on one or more (e.g., distributed) processing devices on a network linking the units FIG. 1. Any of the functions and steps provided in FIGS. 1-9 may be implemented in hardware, software or a combination of both. No claim element herein is to be construed under the provisions of 35 U.S.C. 112, sixth paragraph, unless the element is expressly recited using the phrase "means for."

What is claimed is:

1. A method for determining cardiac output or stroke volume, comprising the activities of:
    receiving, by a processing device, signal data representing a plurality of parameters of a patient, said plurality of parameters being concurrently acquired from a patient over a particular time period and comprising at least two of
        (a) a parameter derived from an ECG waveform of said patient,
        (b) a parameter derived from a blood pressure signal of said patient,
        (c) a parameter derived from signal data representing oxygen content of blood of said patient, and
        (d) a parameter derived from a patient cardiac impedance value;
    combining, by the processing device via a configured artificial neural network, said plurality of parameters and other information of the patient to generate coefficients as output of the artificial neural network, wherein the configured artificial neural network includes weights that are tuned using a training data set including said plurality of concurrently acquired parameters and the coefficients are generated by applying the weights between multiple layers of the artificial neural network;
    calculating, by the processing device, a heart stroke volume of said patient comprising volume of blood transferred through the blood vessel in a heart cycle by determining a summation of the coefficients multiplied by selected parameters of the plurality of concurrently acquired parameters and statistical values of said selected parameters over said particular time period;
    characterizing, by the processing device, cardiac arrhythmia using the calculated heart stroke volume; and
    providing, by the processing device, data representing the characterized cardiac arrhythmia to a destination device.

2. The method according to claim 1, wherein the signal data representing oxygen content of blood of said patient comprises a blood oxygen saturation (SPO2) signal.

3. The method according to claim 1, wherein said plurality of parameters further comprises at least one of, (a) temperature of said patient, (b) invasive blood pressure of said patient, (c) non-invasive blood pressure of said patient and (d) a rate of change of blood pressure of said patient.

4. The method according to claim 1, wherein the statistical values comprise a standard deviation or a higher order statistical value.

5. The method according to claim 1, wherein calculating the heart stroke volume of said patient further comprises using a weighted combination of one or more parameters and a function of a form, $$\sum \text{Vital signs signals\_parameters}(\bullet) = \sum_{i \in ROI\_paramters\_number} \alpha_i(t) \cdot f_i(t)$$

where, Vital signs signals_parameters is a function for calculating indices based on patient parameters, ROI_paramters_number represents a set of integers ranging from 1 to a total number of the patient parameters, $\alpha_i(t)$ represents the coefficient which determines relative contribution from a particular patient parameter, $f_i(t)$ represents the patient parameters, and (t) represents time.

6. The method according to claim 1, including the steps of
    receiving a factor representing reduction in blood flow volume from a patient heart to a particular anatomical location, and
    calculating a heart stroke volume of said patient in response to the factor representing the reduction in blood flow volume from the patient heart to the particular anatomical location.

7. The method according to claim 1, including the step of using predetermined mapping information associating ranges of calculated stroke volume or values derived from said calculated stroke volume with medical conditions and for mapping the calculated stroke volume to data indicating a medical condition of said patient and providing data representing the indicated medical condition to the destination device.

8. A method for determining cardiac output or stroke volume, comprising the activities of:
    receiving, by a processing device, signal data representing a plurality of parameters of a patient including first and second different parameters, said plurality of parameters being concurrently acquired from a patient over a particular time period and comprising at least two of
        (a) a parameter derived from an ECG waveform of said patient,
        (b) a parameter derived from a blood pressure signal of said patient, and
        (c) a parameter derived from signal data representing oxygen content of blood of said patient;
    combining, by the processing device via a configured artificial neural network, said plurality of parameters and other information of the patient to generate coefficients as output of the artificial neural network, wherein the configured artificial neural network includes weights that are tuned using a training data set including said plurality of concurrently acquired parameters and the coefficients are generated by applying the weights between multiple layers of the artificial neural network;
    calculating, by the processing device, a heart stroke volume of said patient comprising volume of blood transferred through the blood vessel in a heart cycle by determining a first summation of values of the coefficients multiplied by the first parameter and a second summation of values of the coefficients multiplied by statistical values of the second parameter, over said particular time period;

characterizing, by the processing device, cardiac arrhythmia using the calculated heart stroke volume; and providing data representing the characterized cardiac arrhythmia to a destination device.

9. The method according to claim 8, wherein the signal data representing oxygen content of blood of said patient comprises a blood oxygen saturation (SPO2) signal.

10. The method according to claim 8, wherein said plurality of parameters further comprises at least one of, (a) temperature of said patient, (b) invasive blood pressure of said patient, (c) non-invasive blood pressure of said patient and (d) a rate of change of blood pressure of said patient.

11. The method according to claim 8, wherein the statistical values comprise a standard deviation or a higher order statistical value.

12. The method according to claim 8, including the steps of
receiving a factor representing reduction in blood flow volume from a patient heart to a particular anatomical location, and
calculating a heart stroke volume of said patient in response to the factor representing the reduction in blood flow volume from the patient heart to the particular anatomical location.

13. The method according to claim 8, including the step of
using predetermined mapping information associating ranges of calculated stroke volume or values derived from said calculated stroke volume with medical conditions and for mapping the calculated stroke volume to data indicating a medical condition of said patient and
providing data representing the indicated medical condition to a destination device.

14. The method according to claim 8, wherein the other information of the patient includes patient demographic data.

15. The method according to claim 14, wherein said demographic data comprises at least two of age, height, weight, gender, and pregnancy status.

16. The method according to claim 8, including the steps of
using predetermined mapping information associating ranges of calculated stroke volume or values derived from said calculated stroke volume with medical conditions and for mapping the calculated stroke volume to data indicating a medical condition of said patient and
providing data representing the indicated medical condition to the destination device wherein said predetermined mapping information associates ranges of the calculated stroke volume with particular patient demographic characteristics and with corresponding medical conditions and
using patient demographic data including at least one of age, weight, gender, and height in comparing the calculated stroke volume with said ranges and generating an alert message indicating a potential medical condition.

17. A system for determining cardiac output or stroke volume, comprising:
an interface configured to receive signal data representing a plurality of parameters of a patient, said plurality of parameters being concurrently acquired from a patient over a particular time period and comprising at least one of
(a) a parameter derived from an ECG waveform of said patient,
(b) a parameter derived from a blood pressure signal of said patient,
(c) a parameter derived from signal data representing oxygen content of blood of said patient and
(d) a parameter derived from a patient cardiac impedance value;
a data processor configured to
generate coefficients as output of a configured artificial neural network based on said plurality of parameters and other information of the patient, wherein the configured artificial neural network includes weights that are tuned using a training data set including said plurality of concurrently acquired parameters and the coefficients are generated by applying the weights between multiple layers of the artificial neural network, and
calculating a heart stroke volume of said patient comprising volume of blood transferred through the blood vessel in a heart cycle, by determining a summation of the generated coefficients multiplied by the selected parameters of the plurality of concurrently acquired parameters over said particular time period and statistical values of said selected parameters;
a detector configured to characterize cardiac arrhythmia using the calculated heart stroke volume; and
an output processor configured to provide data representing the characterized cardiac arrhythmia to a destination device.

18. The system according to claim 17, wherein said data processor calculates said heart stroke volume, in response to, a combination of a weighted summation of values of a first parameter and a weighted summation of values of a second parameter, said summation being over said particular time period and the first and second parameters are selected from said plurality of parameters.

* * * * *